US00PP21795P3

(12) United States Plant Patent
Timmermans et al.

(10) Patent No.: US PP21,795 P3
(45) Date of Patent: Mar. 22, 2011

(54) ***ROSMARINUS* PLANT NAMED 'WILMA'S GOLD'**

(50) Latin Name: *Rosmarinus officinalis*
Varietal Denomination: Wilma's Gold

(76) Inventors: Wilhelmus Timmermans, Haarsteeg (NL); Wilhelmina Timmermans-Peters, Haarsteeg (NL)

( * ) Notice: Subject to any disclaimer, the term of this patent is extended or adjusted under 35 U.S.C. 154(b) by 0 days.

(21) Appl. No.: 12/583,522

(22) Filed: Aug. 22, 2009

(65) Prior Publication Data
US 2011/0047665 P1 Feb. 24, 2011

(51) Int. Cl.
*A01H 5/00* (2006.01)

(52) U.S. Cl. ..... Plt./226

(58) Field of Classification Search ..... Plt./226
See application file for complete search history.

*Primary Examiner* — Susan B McCormick Ewoldt

(57) ABSTRACT

A new and distinct *Rosmarinus* cultivar named 'Wilma's Gold' is disclosed, characterized by solid gold leaves. The new cultivar is a *Rosmarinus*, suitable for ornamental garden purposes.

2 Drawing Sheets

Latin name of the genus and species: *Rosmarinus officinalis.*

Variety denomination: 'WILMA'S GOLD'.

BACKGROUND OF THE INVENTION

The new cultivar is a product of a chance discovery in a commercial setting by the inventors. In the Spring of 2006, the inventors, Wilhelmus Timmermans and Wilhelmina Timmermans-Peters discovered an interesting whole plant mutation in a commercial planting of the unpatented parent variety *Rosmarinus officinalis* 'Blue Rain'. This whole plant mutation occurred was discovered at a commercial nursery in Harsteeg, the Netherlands.

During 2006 the inventors propagated the interesting mutation by vegetative cuttings at the commercial nursery in the Netherlands. The initial propagation showed the mutation to be stable and additional generations were propagated, also by vegetative cuttings. Several generations have been reproduced since 2006, and have shown that the unique features of this cultivar are stable and reproduced true to type.

SUMMARY OF THE INVENTION

The cultivar 'Wilma's Gold' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Wilma's Gold' These characteristics in combination distinguish 'Wilma's Gold' as a new and distinct *Rosmarinus* cultivar:

1. Unique solid gold colored foliage.

COMPARISON TO PARENT VARIETY

Plants of the new cultivar 'Wilma's Gold' are similar to plants of the parent, *Rosmarinus officinalis* 'Blue Rain' in most horticultural characteristics, however, plants of the new cultivar 'Wilma's Gold' have foliage with a solid gold color, whereas plants of 'Blue Rain' produce only green foliage.

COMMERCIAL COMPARISON

Plants of Wilma's Gold' can be compared to the commercial variety *Rosmarianus* 'Gold Dust,' U.S. Plant Pat. No. 19,949. 'Gold Dust' and 'Wilma's Gold' are similar in many characteristics, however, 'Wilma's Gold' has young leaves that are entirely golden yellow, whereas 'Gold Dust' has green with yellow foliage. Additionally, 'Wilma's Gold' has significantly lighter colored flowers than 'Gold Dust.' Additionally 'Wilma's Gold' has a trailing type plant form compared to the upright plant form of 'Gold Dust.' Similar as well is the unpatented variety *Rosmarianus* 'Golden Rain.' However, 'Golden Rain' has a more upright plant form, and leaves which turn green in the Summer months. Comparatively, 'Wilma's Gold' has very golden foliage during the summer, and a more trailing plant form.

BRIEF DESCRIPTION OF THE PHOTOGRAPH

The accompanying photograph in

Figure 1:
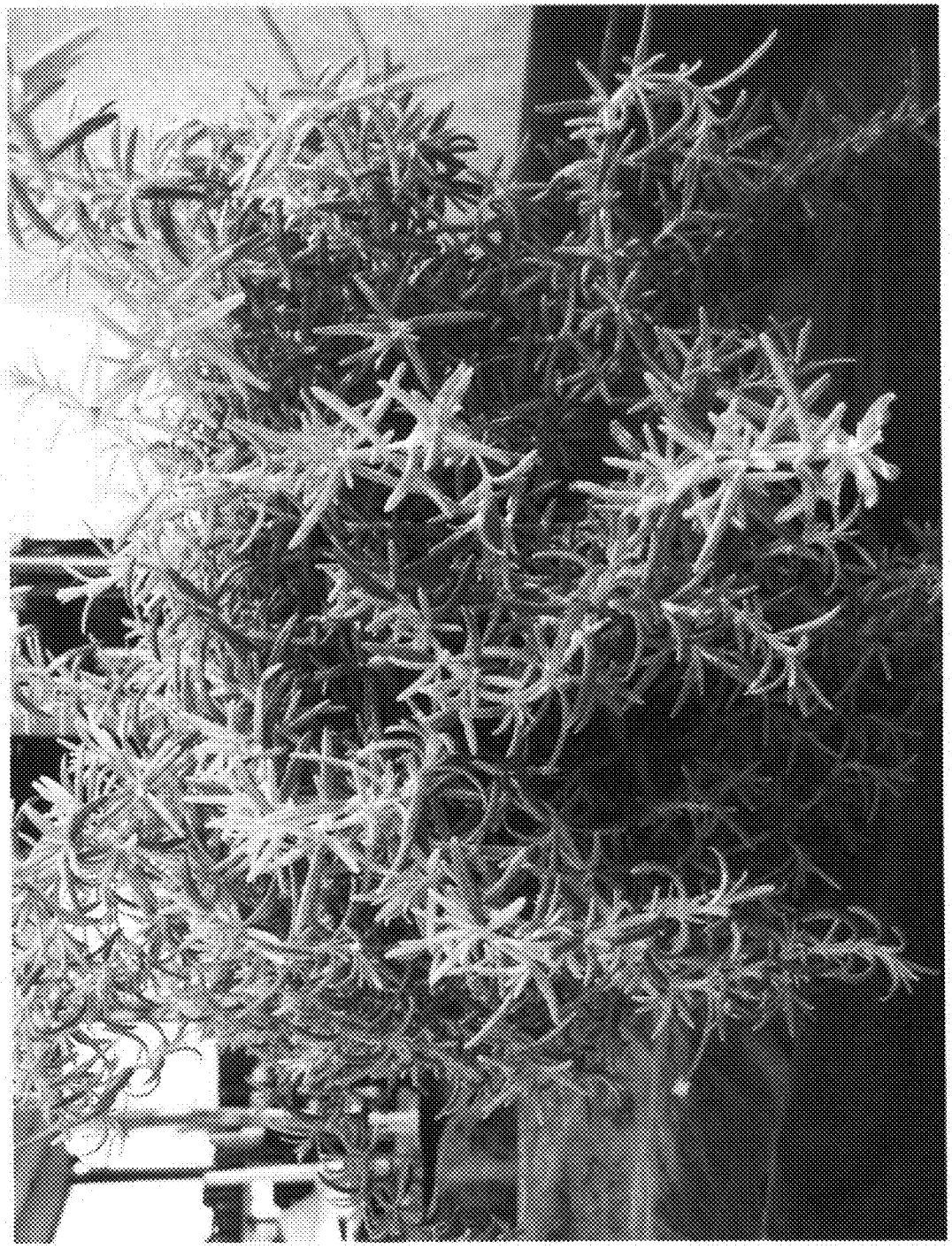
FIG. 1 illustrates in full color a typical plant of 'Wilma's Gold' grown in a greenhouse in the Netherlands. The plant is approximately 18 months old, and is planted in an approximately 20 cm pot.
Figure 2:
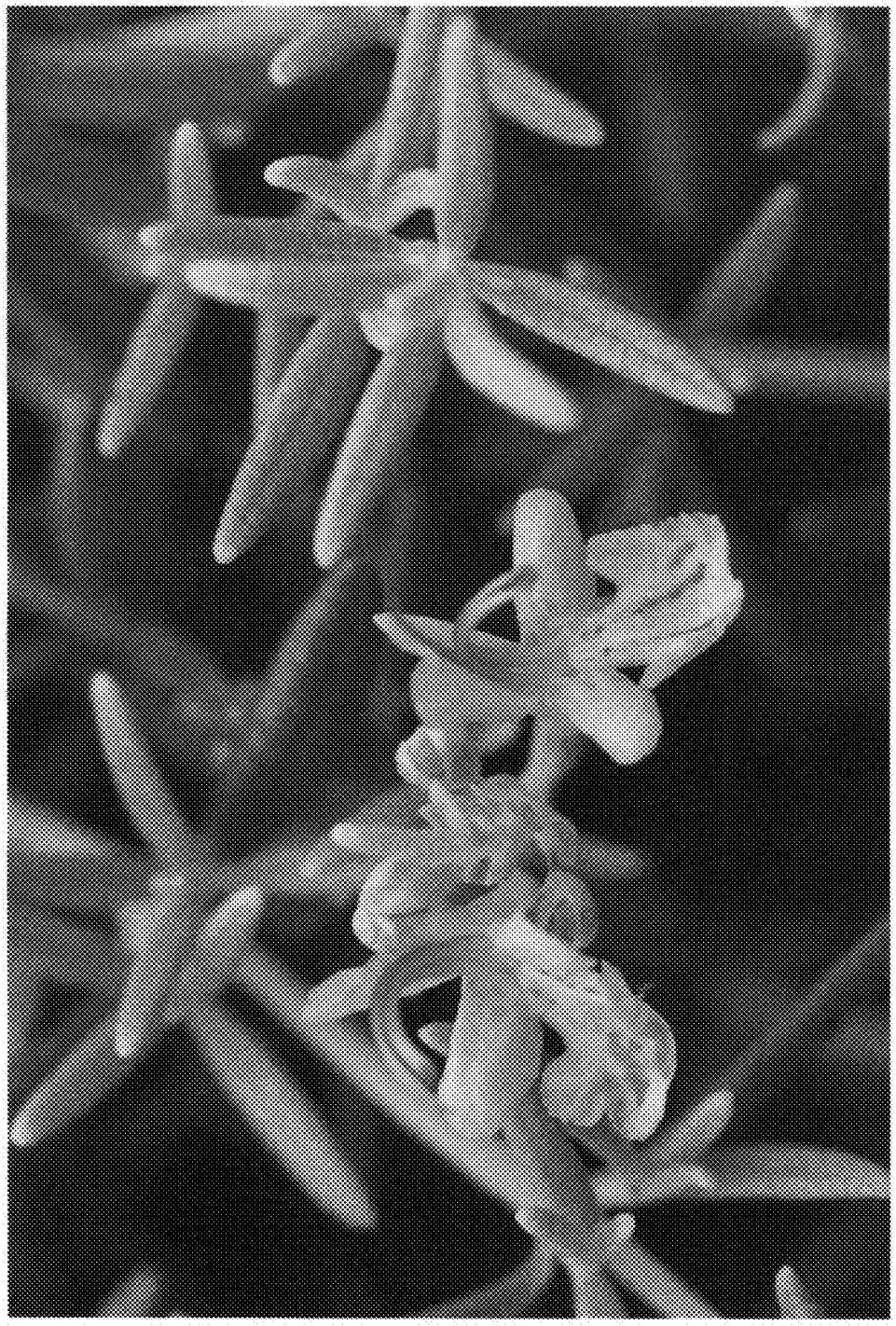
FIG. 2 illustrates in full color typical flowers of 'Wilma's Gold.'

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Wilma's Gold' plants grown in a greenhouse in the netherlands.

Plants are approximately 15 months old, in a 20 cm nursery container. The greenhouse is unheated and unshaded. Temperatures ranged from 2° C. to 20° C. at night to 5° C. to 35° C. during the day. Measurements and numerical values represent averages of typical plant types.

Botanical classification: *Rosmarinus officinalis* 'Wilma's Gold'.

PROPAGATION

Time to initiate roots: About 14-21 days at approximately 20-22° C.

Time to produce a rooted cutting: About 28-56 days at 20-22° C.

Root system: Fibrous.

PLANT

Plant habit: Trailing.

Plant spread: Approximately 37.0 cm.

Plant height: Approximately 22 cm.

Growth rate: Moderate.

Primary stem diameter: Approximately 4 mm.

Primary stem texture: Smooth.

Primary stem color: Between RHS Grey-Brown N199A and Brown N200A.

Any other stem characteristics: No.

Average length of lateral branches: Approximately 21.5 cm.

Average diameter of lateral branches: Approximately 0.2 cm.

Quantity of lateral branches: About 27.

Lateral branch:

- *Color.*—Near RHS 165B, but covered with a dense woolly pubescence.
- *Texture/pubescence.*—Densely woolly pubescent, average length of hairs: 0.02 cm, colored near RHS Green-White 157A.

Internode length: Approximately 1.1 cm.

Age of plant described: Approximately 15 months from a rooted cutting.

FOLIAGE

Leaf:

- *Arrangement.*—Opposite.
- *Quantity.*—Approximately 38 per main branch.
- *Average length.*—Approximately 1.7 cm.
- *Average width.*—Approximately 0.3 cm.
- *Shape of blade.*—Linear.
- *Apex.*—Bluntly acute.
- *Base.*—Narrow attenuate.
- *Attachment.*—Narrow attenuate.
- *Margin.*—Entire, revolute.
- *Texture of top surface.*—Smooth.
- *Pubescence.*—Under side densely woolly pubescent, average length of hairs: 0.02 cm, colored near RHS Green-White 157A, upper side glabrous.
- *Color.*—Young foliage upper side: Near RHS Yellow 2B, base Yellow-Green 145B. Young foliage under side: Near RHS Green-White 157B. Mature foliage upper side: Near RHS Yellow-Green 144A. Mature foliage under side: Near RHS Green-White 157A.
- *Venation.*—Type: Anastomosing. Venation color upper side: Near RHS Green 137B. Venation color under side: Near RHS Green-White 157B.
- *Petiole.*—Average length: Approximately 0.1 cm. Diameter: Approximately 0.1 cm. Color: Near RHS Green-White 157B.

FLOWER

Natural flowering season: Summer.

Inflorescence type and habit: Terminal raceme.

Flower longevity on plant: Approximately 5 days.

Quantity of flowers: About 450 buds and 70 fully opened flowers per plant.

Flower size:

- *Diameter.*—Approximately 1.0 cm.
- *Height.*—Approximately 1.2 cm.

Peduncle:

- *Length.*—0.5 cm.
- *Diameter.*—0.1 cm.
- *Color.*—Near RHS Yellow-Green 150D.
- *Orientation.*—Upright.
- *Strength.*—Moderately strong.

Petals:

- *Petal arrangement.*—Two-lipped; upper lip 2-lobed, lower lip 3-lobed (typical Lamiaceae-shape).
- *Margin.*—Upper lip 2-lobed, lower lip 3-lobed, margins of lobes entire.
- *Tip shape.*—Tips of lobes obtuse, except tip of lower central lobe: emarginate-praemorse.
- *Length.*—Upper lip average: 1.0 cm. Lower lip average: 1.1 cm.
- *Width.*—Upper lip average: 0.6 cm. Lower lip average: 1.0 cm.
- *Petal quantity.*—2.
- *Petal apex shape.*—Apices of lobes obtuse, except tip of lower central lobe: emarginate-praemorse.
- *Texture.*—Smooth.
- *Aspect.*—Upper lip pointed upright, lower lip pointed downward.

Color:

- *Petals.*—When opening: Upper surface: Near RHS Violet-Blue 91B and 91C, lower lip with darker markings; Violet-Blue 92A. Lower surface: Near RHS Violet Blue 92C. Fully opened: Upper surface: Near RHS Violet-Blue 91C, lower lip with darker markings Violet-Blue 92A. Lower surface: Near RHS Violet-Blue 92C. Fading: Near RHS Violet-Blue 91C.

Bud:

- *Shape.*—Obovate.
- *Length.*—Approximately 0.5 cm.
- *Diameter.*—Approximately 0.3 cm.
- *Color.*—Near Violet-Blue RHS 92B, immature sepals colored near RHS Greyed-Purple 187B on upper side and underside a range of both RHS Yellow-Green 144B and 145A.

Sepals:

- *Quantity per flower.*—2; two-lipped; upper lip entire, lower lip 2-lobed.
- *Shape.*—Ovate, lower lip 2-lobed.
- *Length.*—Approximately 0.4 cm.
- *Width.*—Approximately 0.2 cm.
- *Margin.*—Entire.
- *Texture.*—Moderately dense pubescent.

*Color.*—Near RHS Greyed-Purple 187A on upper side and underside a range of both RHS Yellow-Green 144B and 145A.

REPRODUCTIVE ORGANS

Stamens:
*Number.*—2.
*Filament length.*—Approximately 0.9 cm.
Anthers:
*Shape.*—Narrow oblong, dorsifixed.
*Length.*—Approximately 0.1 cm.
*Color.*—Near RHS Blue 102A
*Pollen.*—Color: Near RHS White N155C. Quantity: Low.
Pistil:
*Number.*—1.
*Length.*—Approximately 1.4 cm.
*Style.*—Length: Approximately 1.3 cm. Color: Near RHS Violet-Blue 90B with base near 90D.
*Stigma.*—Shape: Pointed. Color: Near RHS Violet-Blue 94B. Ovary color: Near RHS Yellow-Green 145B.

OTHER CHARACTERISTICS

Seeds and fruits: No fruits/seeds observed to date.
Disease/pest resistance: Neither resistance nor susceptibility to normal pests and diseases of *Rosmarianus* have been observed to date.
Temperature tolerance, high and low: At least hardy to USDA zone 7 (low), high temperature tolerance at least to USDA zone 10.
Drought tolerance: Moderate to moderately high tolerance.
Fragrance: Strong typical Rosmary scent to foliage. Flower fragrance indistinguishable from foliage.

What is claimed is:

1. A new and distinct cultivar of *Rosmarinus* plant named 'Wilma's Gold' as herein illustrated and described.

* * * * *